United States Patent
Park et al.

(10) Patent No.: US 10,959,452 B2
(45) Date of Patent: Mar. 30, 2021

(54) COMPOSITION FOR INDUCED BOWEL MOVEMENT AND DIET AND PREPARATION METHOD THEREOF

(71) Applicant: RG BIO CO., LTD, Daejeon (KR)

(72) Inventors: Se Jin Park, Daejeon (KR); Yoon Ki Min, Daejeon (KR)

(73) Assignee: RG BIO CO., LTD, Daejeon (KR)

(*) Notice: Subject to any disclaimer, the term of this patent is extended or adjusted under 35 U.S.C. 154(b) by 0 days.

(21) Appl. No.: 16/970,483

(22) PCT Filed: Feb. 11, 2019

(86) PCT No.: PCT/KR2019/001602
§ 371 (c)(1),
(2) Date: Aug. 17, 2020

(87) PCT Pub. No.: WO2019/160277
PCT Pub. Date: Aug. 22, 2019

(65) Prior Publication Data
US 2020/0375236 A1    Dec. 3, 2020

(30) Foreign Application Priority Data

Feb. 19, 2018  (KR) ........................ 10-2018-0019117

(51) Int. Cl.
| | | |
|---|---|---|
| A23L 33/135 | (2016.01) | |
| A23L 33/14 | (2016.01) | |
| A23P 10/22 | (2016.01) | |
| A23L 7/10 | (2016.01) | |
| A23L 33/175 | (2016.01) | |
| A23L 33/105 | (2016.01) | |
| A23P 10/28 | (2016.01) | |
| A23L 33/21 | (2016.01) | |
| A61K 31/7016 | (2006.01) | |
| A61K 31/702 | (2006.01) | |
| A61K 35/744 | (2015.01) | |
| A61K 36/03 | (2006.01) | |
| A61K 36/06 | (2006.01) | |
| A61K 36/28 | (2006.01) | |
| A61K 36/68 | (2006.01) | |
| A61K 36/886 | (2006.01) | |
| A61K 36/896 | (2006.01) | |
| A61K 36/899 | (2006.01) | |

(52) U.S. Cl.
CPC ............ *A23L 33/135* (2016.08); *A23L 7/115* (2016.08); *A23L 33/105* (2016.08); *A23L 33/14* (2016.08); *A23L 33/175* (2016.08); *A23L 33/21* (2016.08); *A23P 10/22* (2016.08); *A23P 10/28* (2016.08); *A61K 31/702* (2013.01); *A61K 31/7016* (2013.01); *A61K 35/744* (2013.01); *A61K 36/03* (2013.01); *A61K 36/06* (2013.01); *A61K 36/28* (2013.01); *A61K 36/68* (2013.01); *A61K 36/886* (2013.01); *A61K 36/896* (2013.01); *A61K 36/899* (2013.01); *A61K 2236/13* (2013.01); *A61K 2236/17* (2013.01)

(58) Field of Classification Search
CPC ............................... A61K 36/21; A23L 33/21
USPC .......................................... 426/7, 20; 424/439
See application file for complete search history.

(56) References Cited

U.S. PATENT DOCUMENTS

2016/0089408 A1* 3/2016 Kim .................. A61K 2300/00
435/170

FOREIGN PATENT DOCUMENTS

| KR | 10-2003-0069231 A | 8/2003 |
|---|---|---|
| KR | 10-2003-0096615 A | 12/2003 |
| KR | 10-0545527 B1 | 1/2006 |
| KR | 10-2006-0021247 A | 3/2006 |
| KR | 10-0937455 B1 | 1/2010 |
| KR | 10-2011-0007463 A | 1/2011 |
| KR | 10-1230756 B1 | 2/2013 |
| KR | 10-1450968 B1 | 10/2014 |
| KR | 10-1539382 B1 | 7/2015 |
| KR | 10-1641374 B1 | 7/2016 |
| KR | 10-1911205 B1 | 10/2018 |

OTHER PUBLICATIONS

International Search Report for PCT/KR2019/001602 dated May 14, 2019 (4 pages).

* cited by examiner

*Primary Examiner* — Walter E Webb
(74) *Attorney, Agent, or Firm* — Susan Paik, Esq.

(57) ABSTRACT

The present invention relates to a composition and a healthy food product for inducing bowel movements and promoting weight loss comprising 47-57 parts by weight of a psyllium husk powder, 18-28 parts by weight of a rice bran powder, 5-6 parts by weight of a kelp powder, 4-5 parts by weight of a fructooligosaccharide, 3.5-4.5 parts by weight of chicory fiber, 3-4 parts of weight of glasswort, 2.5-3.5 parts by weight of yeast powder, 1.5-2.5 parts by weight of lactulose powder, 0.5-1.5 parts by weight of lactic acid bacteria powder, 0.05-0.15 parts by weight of complex amino acid, 0.4-0.6 parts by weight of *Aloe arborescens*, and 0.5-1.5 parts by weight of garlic powder. The composition and health food product for inducing bowel movements and promoting weight loss of the present invention comprise nutritional ingredients such as vegetable dietary fiber, vitamins, minerals, etc. which feed beneficial intestinal bacteria.

7 Claims, No Drawings

COMPOSITION FOR INDUCED BOWEL MOVEMENT AND DIET AND PREPARATION METHOD THEREOF

TECHNICAL FIELD

The present invention relates to a composition for inducing defecation and weight loss, and a method for producing the same, and more specifically to a composition for inducing defecation and weight loss that contains psyllium husk, rice bran or the like, containing great amounts of dietary fiber, vitamins and trace elements as main components and thus helps the proliferation of beneficial bacteria in the large intestine and facilitates metabolic activity in the intestine to induce defecation, to provide a sense of satiation and to be effective for weight loss, a health food using the same and a method of producing the same.

BACKGROUND ART

In modern times, nutrients such as proteins and fats cannot be digested and absorbed in the stomach and intestines due to various causes such as excessive consumption of high-calorie nutrient foods, excessive drinking, stress, diseases of the stomach or small intestines, and nutrients that cannot be digested and absorbed are pushed away to the large intestine, located at the end of the digestive system and are then decayed by harmful bacteria in the large intestine, thus producing toxins such as hydrogen sulfide, ammonia, phenol, indole, histamine and amine in the large intestine.

Of these, hydrogen sulfide gas is soluble in water, so it dissolves in the blood and is converted to a sulfate, which causes stress to the liver while detoxifying the sulfate, thereby not only inducing fatigue, headaches and the like, but also inflammation of intestinal wall due to the gas that is dissolved in the blood and is not detoxified in the liver. This inflammation disturbs the immune function and eventually makes the human body vulnerable to disease.

Harmful gases produced in the large intestine is removed in the liver. However, when the liver is unhealthy or harmful gases are excessively generated, the un-detoxified harmful gases degrade the function of the whole body, thereby interrupting normal metabolism and increasing the possibility of the onset of diseases such as ulcerative colitis, Crohn's disease, dermatomyositis and kidney disease.

In addition, the Korea Research Institute of Biomedical Science has reported that, when beneficial bacteria in the intestine are not activated, metabolism for serotonin synthesis cannot be performed, indices of stress become more severe, and mental disorders such as depression and anger management disorders occur. It has also been found that harmful bacteria in the intestine cause diarrhea, abdominal pain, constipation and toxic gases, resulting in inflammation, thus disturbing immune function and worsening arteriosclerosis.

Conventionally, when a problem occurs in the large intestine, for example, when constipation occurs, a therapeutic agent is administered for treatment, but, disadvantageously, such treatment is not a preventive action, but is used only after an abnormality occurs in the large intestine.

As preventive approaches, there are methods such as Korean Patent No. 10-1450968 entitled "Health food composition for improving regular bowel movements to alleviate constipation and coprostasis", Korean Patent Laid-open No. 10-2003-0069231 entitled "Composition for improving intestinal function depending on constipation type", and Korean Patent No. 10-1230756 entitled "Natural food composition prescribed for skinny type". However, these methods include mixing with lactic acid bacteria, among the beneficial bacteria in the intestine, but the lactic acid bacteria cannot reach the beneficial intestinal bacteria while remaining alive. In addition, the methods further require the process of inoculating various lactic acid bacteria in the process of mixing the composition, thus causing a problem of cost increase.

Meanwhile, psyllium husks are not digested in the human digestive system, but reach the large intestine due to the high content of water-insoluble dietary fiber, and thus is fed to the beneficial bacteria in the large intestine, thereby promoting the intestinal environment of the large intestine and facilitating peristalsis of the large intestine due to proliferation of the beneficial bacteria. Dietary fibers of psyllium husk increase the volume by up to 40 times when absorbing moisture, forming porous fibers and increasing the volume and water content of the stool. Thus, psyllium husks are effective in preventing hard stool containing little moisture and in relieving the proctodynia caused by hemorrhoids or bowel movements.

Rice bran including an embryo bud of rice contains complete nutrients and metabolites for germination. As used herein, the term "rice bran" is generally defined by including an embryo bud of rice and rice bran. Vitamin B1 (thiamine) in rice bran is a substance involved in glucose metabolism of amylase, which is a metabolite that breaks down rice, which contains, as a main ingredient, carbohydrate, as a polysaccharide, to glucose which is a monosaccharide as an essential nutrient for the human body, and vitamin B6 (pyridoxine) is a substance involved in an amino acid metabolism of protein. In particular, the GABA component and octacosanol are foods of *Bifidobacterium* among microorganisms in the intestine, and *Bifidobacterium* is particularly abundant in the intestines of breastfeeding infants, and proliferates using oligosaccharides that are not available to harmful pathogens. *Bifidobacterium* is well known not to produce methane gas. In addition, this component has functions of capturing and discharging triglycerides in the intestine and thus acting as a lubricant to apply an oil to stools during defecation to promote defecation.

Meanwhile, rice bran has a problem of early deterioration, in which rancidity starts within a few hours after rice milling, and contains a lot of polysaccharides that are not easily digested, and thus has a low actual utilization rate in the body despite containing high amounts of vitamins and nutrients. Therefore, rice bran is widely used in conventional diet foods and healthy foods to induce defecation. However, it is difficult to incorporate a large amount of rice bran in these foods and it is also difficult to realize the function of the rice bran when incorporated therein.

PRIOR ART DOCUMENT

Patent Document (Patent Document 1) Korean Patent No. 10-1450968
(Patent Document 2) Korean Patent Laid-open No. 10-2003-0069231
(Patent Document 3) Korean Patent No. 10-1230756
(Patent Document 4) Korean Patent No. 10-0545527
(Patent Document 5) Korean Patent Laid-open No. 10-2006-0021247

SUMMARY OF THE INVENTION

Technical Problem

It is an object of the present invention to provide a composition for inducing defecation and weight loss that contains psyllium husk, rice bran or the like, containing large amounts of dietary fiber, vitamins and trace elements as main components, and thus helps the proliferation of beneficial bacteria in the large intestine and facilitates metabolic activity in the intestine to induce defecation, and provides nutrients necessary for the human body such as vitamins, trace elements, etc. with low calories and provides a sense of satiation to be effective for weight loss, a health food using the same, and a method of producing the same.

Technical Solution

In accordance with one aspect of the present invention, the above and other objects can be accomplished by the provision of a composition for inducing defecation and promoting weight loss containing 47 to 57 parts by weight of a psyllium husk powder, 18 to 28 parts by weight of a rice bran powder, 5 to 6 parts by weight of a kelp powder, 4 to 5 parts by weight of a fructooligosaccharide, 3.5 to 4.5 parts by weight of a chicory fiber, 3 to 4 parts of weight of glasswort (*Salicornia europaea* L.), 2.5 to 3.5 parts by weight of a yeast powder, 1.5 to 2.5 parts by weight of a lactulose powder, 0.5 to 1.5 parts by weight of a lactic acid bacteria powder, 0.05 to 0.15 parts by weight of complex amino acid, 0.4 to 0.6 parts by weight of *Aloe arborescens*, and 0.5 to 1.5 parts by weight of a garlic powder.

In the composition, the rice bran is preferably brown rice bran, white rice bran, or a mixture of brown rice bran and white rice bran.

In an embodiment of the present invention, the rice bran is preferably produced by a method including washing the rice bran, sterilizing the washed rice bran at a temperature of 120° C. for 30 minutes or more by a method selected from high-temperature steam sterilization, ultraviolet sterilization, and far-infrared sterilization, and drying the sterilized rice bran to a water content of 5% or less in a drying chamber at 55 to 65° C.

In another embodiment of the present invention, the rice bran is preferably produced by a method including washing the rice bran, sterilizing the washed rice bran at a temperature of 120° C. for 30 minutes or more by a method selected from high-temperature steam sterilization, ultraviolet sterilization, and far-infrared sterilization, inoculating the washed and sterilized rice bran with a *Bacillus* strain or an *Aspergillus* strain, fermenting the resulting rice bran for 36 hours or more at a humidity of 60 to 80% and a temperature of 30 to 50° C., and drying the fermented rice bran in a drying chamber at 55 to 65° C. to a water content of 5% or less.

In addition, the present invention provides a method for producing a health food for inducing defecation and promoting weight loss, including:

preparing sterilized and dried raw materials including psyllium husk, rice bran, kelp, fructooligosaccharide, a chicory fiber, glasswort (*Salicornia europaea* L.), yeast, lactulose, a lactic acid bacteria, complex amino acid, *Aloe arborescens* and garlic, and powderizing the raw materials to a certain size;

mixing predetermined amounts of the resulting raw materials with each other, particularly 47 to 57 parts by weight of a psyllium husk powder, 18 to 28 parts by weight of a rice bran powder, 5 to 6 parts by weight of a kelp powder, 4 to 5 parts by weight of a fructooligosaccharide, 3.5 to 4.5 parts by weight of a chicory fiber, 3 to 4 parts of weight of glasswort (*Salicornia europaea* L.), 2.5 to 3.5 parts by weight of a yeast powder, 1.5 to 2.5 parts by weight of a lactulose powder, 0.5 to 1.5 parts by weight of a lactic acid bacteria powder, 0.05 to 0.15 parts by weight of complex amino acid, 0.4 to 0.6 parts by weight of *Aloe arborescens*, and 0.5 to 1.5 parts by weight of a garlic powder to obtain a raw material mixture, and mixing 55 to 65 parts by weight of drinking water or purified water based on 100 parts by weight of the raw material mixture and kneading the resulting materials;

molding the resulting paste into a granule or a pill; and drying the molded granule or pill using a fluid bed dryer to adjust the water content to 5% by weight or less.

In the method, the rice bran is preferably produced by a method including washing the rice bran, sterilizing the washed rice bran at a temperature of 120° C. for 30 minutes or more by a method selected from high-temperature steam sterilization, ultraviolet sterilization, and far-infrared sterilization, and drying the sterilized rice bran to a water content of 5% or less in a drying chamber at 55 to 65° C.

In another embodiment, the rice bran is preferably produced by a method including washing the rice bran, sterilizing the washed rice bran at a temperature of 120° C. for 30 minutes or more by a method selected from high-temperature steam sterilization, ultraviolet sterilization, and far-infrared sterilization, inoculating the washed and sterilized rice bran with a *Bacillus* strain or an *Aspergillus* strain, fermenting the resulting rice bran for 36 hours or more at a humidity of 60 to 80% and a temperature of 30 to 50° C., and drying the sterilized rice bran in a drying chamber at 55 to 65° C. to a water content of 5% or less.

In accordance with another aspect of the present invention, provided is a health food for inducing defecation and promoting weight loss containing the composition.

Advantageous Effects

The composition and health food for inducing defecation and promoting weight loss according to the present invention include nutrients such as vegetable dietary fiber, vitamins, minerals, etc., which feed the beneficial bacteria in the intestine, thereby activating beneficial bacteria in the intestine, increasing the ratio of beneficial bacteria in the intestinal flora, and promoting intestinal metabolism, inducing defecation and preventing the generation of toxins in the intestine.

When ingested with water, the composition and health food expand to provide a sense of satiation, thereby discouraging the consumption of excessive amounts of food and enabling complete metabolism of nutrients in the food consumed, preventing the generation of toxins in the intestine, preventing diseases caused by toxins in the intestine, and providing nutrients such as vitamins—trace elements, etc. necessary for the human body, and thus being effective in weight loss.

Also, the composition and health food have effects in that the speed of defecation upon defecation is fast, the fiber is abundant, so the feces float in water, and after defecation, the feces do not stick to tissue, there is no sensation of incomplete evacuation and there is ultimately an effect of finally observe gold feces within 1 month.

In addition, the health food produced in the form of a granule or pill is convenient to carry and eat, and controlling the size and amount of the pill induces water consumption when ingested so as to encourage consumption of sufficient water every day.

DETAILED DESCRIPTION

Best Mode

The composition according to the present invention contains 47 to 57 parts by weight of a psyllium husk powder, 18 to 28 parts by weight of a rice bran powder, 5 to 6 parts by weight of a kelp powder, 4 to 5 parts by weight of a fructooligosaccharide, 3.5 to 4.5 parts by weight of a chicory fiber, 3 to 4 parts of weight of glasswort (*Salicornia europaea* L.), 2.5 to 3.5 parts by weight of a yeast powder, 1.5 to 2.5 parts by weight of a lactulose powder, 0.5 to 1.5 parts by weight of a lactic acid bacteria powder, 0.05 to 0.15 parts by weight of complex amino acid, 0.4 to 0.6 parts by weight of *Aloe arborescens*, and 0.5 to 1.5 parts by weight of a garlic powder.

The psyllium husk is rich in water-insoluble dietary fiber, thus having effects of promoting peristaltic motion of the large intestine, and increasing the volume and water content of feces since the volume thereof increases when absorbing moisture, thereby inducing and promoting defecation.

Rice bran including an embryo bud of rice contains complete nutrients and metabolites for germination. As used herein, the term "rice bran" is generally defined by including an embryo bud of rice and rice bran. Rice bran is classified into brown bran, produced by primary rice milling (1-3 times), and white bran, produced by the subsequent rice milling (3-7 times), to obtain white rice after the primary rice milling.

The rice bran is rich in vitamin B1 (thiamine), which is involved in glucose metabolism of amylase, which breaks down carbohydrates, and vitamin B6 (pyridoxine), which is involved in amino acid metabolism of proteins. In particular, the embryo bud of rice contains great amounts of metabolites, also called nutrient regulators, such as GABA, vitamin B1, vitamin B6, octacosanol, mineral groups, phytic acid, beta-sterol, etc. which act on sugar metabolism, and rice bran contains, as a main ingredient, water-soluble dietary fiber, which is a food for beneficial bacteria in the large intestine.

The brown rice bran obtained through the primary rice-milling process contains a large amount of an embro bud of rice, and white rice bran contains a large amount of rice bran. Thus, if necessary, brown rice or white rice may be used alone, or a mixture thereof may be used.

In the case where a mixture of brown rice and white rice is used, brown rice and white rice are preferably used at a weight ratio of 1:3 to 3:1, but the disclosure is not particularly limited thereto.

In addition, the rice is preferable *Japonica* rice or Indica rice, and more preferably Indica rice. Starch, which is the main ingredient of rice, includes α starch and β starch. β starch is converted to α starch, which is digested only when the temperature is high. *Japonica* rice contains a great amount of β-starch and thus is elastic, but digestion thereof is difficult when eaten cold, and *Japonica* rice contains a great amount of vegetable oil and thus is glossy, and so often needs to be degreased when produced into as a functional food. On the other hand, Indica rice has a high α starch content and low vegetable oil content and thus is neither glossy nor elastic, but digestion thereof is easy even when eaten cold. Thus, Indica rice bran is preferably used when it is difficult to digest brown rice. Therefore, Indica rice bran can exert excellent functional effects without degreasing or high-temperature fermentation.

The rice bran is used in the form of an unfermented rice bran powder or a fermented rice bran powder.

The rice bran powder is preferably prepared by the following method.

First, as a raw material, a brown rice powder, a white rice powder, or a mixture thereof is used.

The raw material is washed and then sterilized. The washing is preferably carried out using steam. The sterilization is preferably carried out by high-temperature steam sterilization, ultraviolet sterilization or far-infrared sterilization at 120° C. for 30 minutes or longer. At this time, it is more preferable to perform far-infrared sterilization or ultraviolet sterilization since high-temperature sterilization may destroy the vitamins contained in the rice bran.

The sterilized rice bran is dried in a drying chamber at about 60° C. to a water content of 5% or less. Drying enables the rice bran powder to be maintained in a stable state.

Through the above process, lipase is inactivated, thus solving the problem of rancidity of rice bran, sterilizing the raw materials in a sanitary manner, and maintaining a stable state.

The rice bran powder treated as above is particularly suitable for health food targeting young people with good digestion.

The fermented rice bran powder is preferably prepared by the following method.

First, as a raw material, a brown rice powder, a white rice powder, or a mixture thereof is used.

The raw material is washed and then sterilized. The washing is preferably carried out using steam. The sterilization is preferably carried out by high-temperature steam sterilization, ultraviolet sterilization or far-infrared sterilization at 120° C. for 30 minutes or longer. Here, it is more preferable to perform far-infrared sterilization or ultraviolet sterilization, since high-temperature sterilization may destroy the vitamins contained in the rice bran.

The washed and sterilized rice bran is put in a fermentation chamber and inoculated with *Bacillus* strain or *Aspergillus* strain as a fermentation strain, and fermented for 36 hours or more at a humidity of 60 to 80% and a temperature of 30 to 50° C. At this time, it is preferable to inoculate the rice bran with about 5±3% of a fermentation strain per kg of the rice bran. Although not particularly limited, *Bacillus subtilis, Bacillus natto* or the like may be used as the *Bacillus* strain, and *Aspergillus niger* or *Aspergillus oryzae* may be used as the *Aspergillus* strain. The strains may be used alone or in combinations of two or more, or may be mixed with another fermentation strain.

Through this fermentation process, indigestible polysaccharides are degraded to monosaccharides, fat components are degreased and are converted into rice bran, which is easily digested and absorbed, and absorption of other nutrients is also facilitated.

The sterilized rice bran is dried in a drying chamber at about 60° C. to a water content of 5% or less. The strains used for fermentation remain dormant due to the drying process.

The fermented rice bran powder treated as above is particularly suitable for health foods targeting persons with poor digestion or elderly people, and is preferable to rice bran powder in terms of absorption of nutrients.

Kelp is rich in potassium and alginic acid, which helps to release LDL, which is a form of cholesterol that is harmful to human bodies, and is suitable for weight loss due to the low-calorie thereof.

Fructooligosaccharides are fermented by intestinal bacteria in the large intestine, promote the proliferation of beneficial bacteria, suppress the growth of harmful bacteria, facilitate bowel movements and help absorb calcium.

Chicory is a plant in the family Asteraceae, and chicory fiber is rich in dietary fiber, iron, carotene, and minerals necessary for nutritional balance and bowel activity, and is thus effective in defecation such as digestion and diuresis.

*Salicornia europaea* L. relieves nutritional imbalances that may occur during dieting and helps in bowel activity.

A yeast powder, a lactulose powder, a lactic acid bacteria powder, complex amino acid, *Aloe arborescens* and a garlic powder are components for compensating for nutrient imbalance or supplementing essential enzymes.

The composition has no tolerance and thus can be administered whenever necessary, such as before or after eating, before or after drinking, or when fasting.

The composition may be used in a powder form, or may be prepared as a health food in the form of a granule or pill. When prepared in the form of a granule or pill, the composition is easy to store and administer.

It is preferable to adjust the dose to 5 g or more and increase the volume so that a large amount of water is consumed when administered.

A method of producing a healthy food for inducing defecation and promoting weight loss according to the present invention includes preparing raw materials and pulverizing (powderizing) the same to a predetermined size, mixing the powdered raw materials in a certain ratio and kneading the same, molding the result into a granule or a pill formulation, and drying the same.

Powderizing

First, as raw materials, psyllium husk, fermented rice bran, kelp, a fructooligosaccharide, a chicory fiber, glasswort (*Salicornia europaea* L.), yeast, lactulose, a lactic acid bacteria, complex amino acid, *Aloe arborescens* and garlic are prepared in the form of sterilized and dried powders.

Preferably, whether or not the prepared raw materials are decayed or contaminated by harmful bacteria is tested.

The prepared raw materials are powderized (pulverized) to a certain size. The powderizing is preferably carried out by powderizing the raw material to a particle size of 40±10 mesh, particularly preferably a particle size of 40 mesh. When the particle size was 40 mesh, water swelling was the best and swallowing was excellent when ingested.

Mixing and Kneading Raw Materials

The powdered raw materials in the step above are weighed in the following amounts: 47 to 57 parts by weight of a psyllium husk powder, 18 to 28 parts by weight of a rice bran powder or a fermented rice bran powder, 5 to 6 parts by weight of a kelp powder, 4 to 5 parts by weight of a fructooligosaccharide, 3.5 to 4.5 parts by weight of a chicory fiber, 3 to 4 parts of weight of glasswort (*Salicornia europaea* L.), 2.5 to 3.5 parts by weight of a yeast powder, 1.5 to 2.5 parts by weight of a lactulose powder, 0.5 to 1.5 parts by weight of a lactic acid bacteria powder, 0.05 to 0.15 parts by weight of complex amino acid, 0.4 to 0.6 parts by weight of *Aloe arborescens*, and 0.5 to 1.5 parts by weight of a garlic powder, and then mixed. At this time, it is preferable to accurately measure the weight using an electronic balance.

The resulting mixture is kneaded while homogeneously mixing with sterilized drinking water or purified water. At this time, it is preferable to mix 55 to 65 parts by weight of drinking water or purified water based on 100 parts by weight of the total raw material.

In addition, it is preferable to conduct mixing using a mixer such as a Y-type mixer, a speed mixer, or the like.

Molding

The paste is molded into a granule or pill.

At this time, the size of the granule is preferably 0.3 mm to 0.5 mm in diameter and 3 to 5 mm in length, and the size of the pill is preferably 3 mm to 5 mm in diameter.

Drying

The molded granule or pill formulation is dried using a fluidized bed dryer to adjust the water content to 5% by weight or less.

Preferably, the dried granule or pill formulation obtained through the above process is regulated to obtain a uniform particle size and treated to obtain an even surface roughness. It is preferable to treat the granule or pill formulation using Powermill.

The particle size of the molded product is screened using a three-stage vibrator.

The product having the screened particle size is packaged and subjected to a quality inspection process that includes visual inspection and detection of harmful bacteria through sampling inspection and is then ready for shipping.

The composition for inducing defecation and promoting weight loss according to the present invention may be prepared into various formulations and used as a health food for inducing defecation and promoting weight loss.

As used herein, the term "health food" is generally defined as a food that a consumer consumes based on the expectation of functionality to obtain a useful effect on health, such as regulation of nutrients or a physiological action with respect to the structure and function of the human body, and includes all of what are commonly referred to as "health functional food", "health food", and "functional food", without limitation to legal regulations.

The health food containing the composition according to the present invention, specifically, may be produced into a health food formulation in the form of a granule or pill through the production method described above, but is not limited thereto, and may be prepared into various formulations as necessary. For example, the health food may be formulated into a tablet, capsule, powder, liquid or the like, in addition to a granule or pill.

EXAMPLES FOR INVENTION

Hereinafter, the present invention will be described in more detail with reference to examples. However, the examples are provided only for illustration of the present invention, and should not be construed as limiting the scope of the present invention.

Example 1

52 g of a psyllium husk powder, 22.9 g of a fermented rice bran powder, 5.5 g of a kelp powder, 4.5 g of fructooligosaccharide, 4 g of a chicory fiber, 3.5 g of glasswort (*Salicornia europaea* L.), 3 g of a yeast powder, 2 g of a lactulose powder, 1 g of a lactic acid bacteria powder, 0.1 g of complex amino acid, 0.5 g of *Aloe arborescens*, and 1 g of a garlic powder were mixed to prepare a composition for inducing defecation and promoting weight loss.

Example 2

52 g of a psyllium husk powder, 22.9 g of a rice bran powder, 5.5 g of a kelp powder, 4.5 g of fructooligosaccharide, 4 g of a chicory fiber, 3.5 g of glasswort (*Salicornia europaea* L.), 3 g of a yeast powder, 2 g of a lactulose powder, 1 g of a lactic acid bacteria powder, 0.1 g of complex amino acid, 0.5 g of *Aloe arborescens*, and 1 g of a garlic powder were mixed to prepare a composition for inducing defecation and promoting weight loss.

Example 3

First, as raw materials, psyllium husk, fermented rice bran, kelp, a fructooligosaccharide, a chicory fiber, glasswort (*Salicornia europaea* L.), yeast, lactulose, a lactic acid bacteria, complex amino acid, *Aloe arborescens* and garlic were prepared in the form of sterilized and dried powders.

In the test process of the raw material, an *E. coli* test was performed to determine whether or not the raw material was decayed and contaminated by harmful bacteria.

After the test, 52 g of a psyllium husk powder, 22.9 g of a fermented rice bran powder, 5.5 g of a kelp powder, 4.5 g of a fructooligosaccharide, 4 g of a chicory fiber, 3.5 g of glasswort (*Salicornia europaea* L.), 3 g of a yeast powder, 2 g of a lactulose powder, 1 g of a lactic acid bacteria powder, 0.1 g of complex amino acid, 0.5 g of *Aloe arborescens*, and 1 g of a garlic powder were weighed.

The desired particle size of the weighted raw material was obtained by screening through a 40 mesh screen.

100 g of the raw material was mixed with about 60 g of purified water and kneaded while the raw materials were mixed to homogeneity using a Y-type mixer.

When the kneading was completed, the paste was molded into a pill having a diameter of 3 mm, and the pill was dried in a fluidized bed dryer so that the water content was adjusted to 5% by weight or less.

Using Powermill, the particle size of the dried pill product was regulated uniformly and the dried pill product was treated to obtain an even surface roughness.

The resulting product was sorted according to particle size by screening using a three-stage vibrator.

Experimental Example 1

The following test was conducted in order to determine the effects of the composition of the present invention.

100 adult males and females who suffer from diarrhea, abdominal pain, sensation of incomplete evacuation and frequent defecation after drinking alcohol were administered with 30 g of the pill prepared in Example 3 above and consumed one bottle of Soju or 1,000 cc of beer. Then, whether or not symptoms upon the first subsequent defecation were alleviated was determined. The results are shown in Table 1 below. Here, severe diarrhea and severe abdominal pain indicate symptoms and pain severe enough to require medicine.

TABLE 1

Condition of Experimental Group subjects (diarrhea, abdominal pain and sensation of incomplete evacuation after drinking alcohol, number of defecations per day)

| Symptoms and conditions | Before administration | | After administration | |
|---|---|---|---|---|
| Diarrhea | Severe diarrhea | 37 | Good | 51 |
| | Diarrhea | 63 | Excellent | 49 |

TABLE 1-continued

Condition of Experimental Group subjects (diarrhea, abdominal pain and sensation of incomplete evacuation after drinking alcohol, number of defecations per day)

| Symptoms and conditions | Before administration | | After administration | |
|---|---|---|---|---|
| Abdominal pain | Severe abdominal pain | 21 | Good | 56 |
| | Abdominal pain | 79 | Excellent | 44 |
| Sensation of incomplete evacuation | Severe sensation of incomplete evacuation | 67 | Good | 47 |
| | Sensation of incomplete evacuation | 33 | Excellent | 53 |
| Number of defecations per day | 3 or less | 78 | 1 | 43 |
| | 3 or more | 22 | Not less than 2 and less than 3 | 57 |

As can be seen from the results in Table 1, after administrating the composition of the present invention, the number of occurrences of diarrhea, abdominal pain, sensation of incomplete evacuation and number of defecations per day after drinking were greatly improved.

Experimental Example 2

The following test was conducted in order to determine the effect of the composition of the present invention on constipation.

First, as shown in Table 2 below, the test subjects were 100 adults of males and females currently administered with a drug for treating or alleviating constipation, and the numbers of males and females were 30 and 70, respectively.

TABLE 2

Test subjects (100 adult males and females currently administered with a drug for treating or alleviating constipation) Multiple responses possible

| | Gender | |
|---|---|---|
| Symptoms | Male (30) | Female (70) |
| Less than 1 defecation every 3 days | 20 | 63 |
| Hard and dark-blue feces | 25 | 52 |
| Sensation of incomplete evacuation | 27 | 65 |
| Total | 72 | 180 |

Tables 3 to 5 below show the results of observing the change over 3 days after the subjects were administered with 10 g of the pill prepared in Example 3 three times a day before meals for 3 days.

TABLE 3

| | Gender | | | | | |
|---|---|---|---|---|---|---|
| | Male (30) | | | Female (70) | | |
| Symptoms | one or more per day | one or more every 2 days | one or more every 3 days | one or more per day | one or more every 2 days | one or more every 3 days |
| The number of defecations per day | 17 | 7 | 4 | 46 | 13 | 6 |

As can be seen from the results of Table 3 above, which shows the number of defecations per day, 17 out of 30 males and 46 out of 70 females defecated one or more times a day.

TABLE 4

| Symptoms | Male (30) | | | | | | Female (70) | | | | | |
|---|---|---|---|---|---|---|---|---|---|---|---|---|
| | Softening | | | Change in color (yellow) | | | Softening | | | Change in color (yellow) | | |
| | 1 day | 2 days | 3 days | 1 day | 2 days | 3 days | 1 day | 2 days | 3 days | 1 day | 2 days | 3 days |
| Hard and dark-blue feces | 11 | 5 | 8 | 6 | 5 | 10 | 34 | 17 | 11 | 28 | 15 | 19 |

As can be seen from the results of Table 4 above, which showed the hardness and color of feces, an improvement effect was observed from the 1$^{st}$ day of administration, and after 3 days, the effect of softening the feces and the effect of improving color from dark blue to yellow in a number of test subjects was determined.

TABLE 5

| | Gender | | | | | |
|---|---|---|---|---|---|---|
| | Male (30) Sensation of incomplete evacuation disappears | | | Female (70) Sensation of incomplete evacuation disappears | | |
| Symptoms | 1 day | 2 days | 3 days | 1 day | 2 days | 3 days |
| Sensation of incomplete evacuation | 8 | 11 | 7 | 24 | 22 | 15 |

As can be seen from the results of Table 5, which show the sensation of incomplete evacuation, an improvement was observed from the first day of administration, and after 3 days, it can be seen that the sensation of incomplete evacuation disappeared in a large number of test subjects. It can be seen from the results of Tables 3 to 5 that when the composition of the present invention is administered, an effect of alleviation of constipation symptoms appears in a short period of time.

Experimental Example 3

The following test was conducted in order to determine the effect of the composition of the present invention on obesity.

The test subjects were 50 adult males and females with obesity, and the numbers of males and females were 20 and 30, respectively.

Table 6 shows the results of observing the change over 45 days after the subjects were administered with 10 g of the pill prepared in Example 3 three times a day before meals for 45 days.

TABLE 6

| Gender | | | | | | |
|---|---|---|---|---|---|---|
| Male (20) Decrease in body fat loss of 2 kg or more | | | Female (30) Decrease in body fat loss of 2 kg or more | | | |
| 15 days | 30 days | 45 days | 15 days | 30 days | 45 days |
| 1 | 5 | 12 | 2 | 7 | 18 |

As can be seen from the results of Table 6, after 45 days, most subjects lost 2 kg or more of body fat.

The invention claimed is:

1. A composition for inducing defecation and promoting weight loss comprising:
   47 to 57 parts by weight of a psyllium husk powder; 18 to 28 parts by weight of a rice bran powder;
   5 to 6 parts by weight of a kelp powder;
   4 to 5 parts by weight of a fructooligosaccharide;
   3.5 to 4.5 parts by weight of a chicory fiber;
   3 to 4 parts of weight of glasswort (*Salicornia europaea* L.);
   2.5 to 3.5 parts by weight of a yeast powder;
   1.5 to 2.5 parts by weight of a lactulose powder;
   0.5 to 1.5 parts by weight of a lactic acid bacteria powder;
   0.05 to 0.15 parts by weight of complex amino acid;
   0.4 to 0.6 parts by weight of *Aloe arborescens*; and 0.5 to 1.5 parts by weight of a garlic powder,
   wherein the rice bran is produced by a method including washing rice bran, sterilizing the washed rice bran at a temperature of 120° C. for 30 minutes or more by a method selected from high-temperature steam sterilization, ultraviolet sterilization and far-infrared sterilization, and drying the sterilized rice bran to a water content of 5% or less in a drying chamber at 55 to 65° C.

2. The composition according to claim 1, wherein the rice bran is a fermented rice bran obtained by a method further including, before drying, inoculating the sterilized rice bran with a *Bacillus* strain or an *Aspergillus* strain and fermenting the resulting rice bran for 36 hours or more at a humidity of 60 to 80% and a temperature of 30 to 50° C.

3. The composition according to claim 1, wherein the rice bran is brown rice bran, white rice bran, or a mixture of brown rice bran and white rice bran.

4. A method for producing a health food for inducing defecation and promoting weight loss, comprising:
   preparing sterilized and dried powder forms of raw materials including psyllium husk, rice bran, kelp, fructooligosaccharide, a chicory fiber, glasswort (*Salicornia europaea* L.), yeast, lactulose, a lactic acid bacteria, complex amino acid, *Aloe arborescens* and garlic, and powderizing the raw materials to a certain size;

mixing the resulting powderized raw materials in amounts of 47 to 57 parts by weight of a psyllium husk powder, 18 to 28 parts by weight of a rice bran powder, 5 to 6 parts by weight of a kelp powder, 4 to 5 parts by weight of a fructooligosaccharide, 3.5 to 4.5 parts by weight of a chicory fiber, 3 to 4 parts of weight of glasswort (*Salicornia europaea* L.), 2.5 to 3.5 parts by weight of a yeast powder, 1.5 to 2.5 parts by weight of a lactulose powder, 0.5 to 1.5 parts by weight of a lactic acid bacteria powder, 0.05 to 0.15 parts by weight of complex amino acid, 0.4 to 0.6 parts by weight of *Aloe arborescens*, and 0.5 to 1.5 parts by weight of a garlic powder to obtain a raw material mixture, mixing 55 to 65 parts by weight of drinking water or purified water based on 100 parts by weight of the raw material mixture and kneading the resulting material;

molding the resulting paste into a granule or a pill; and drying the molded granule or pill using a fluid bed dryer to adjust a water content to 5% by weight or less, wherein the rice bran is produced by a method including washing rice bran, sterilizing the washed rice bran at a temperature of 120° C. for 30 minutes or more by a method selected from high-temperature steam sterilization, ultraviolet sterilization and far-infrared sterilization, and drying the sterilized rice bran to a water content of 5% or less in a drying chamber at 55 to 65° C.

5. The method according to claim 4, wherein the rice bran is a fermented rice bran obtained by a method further including, before drying, inoculating the sterilized rice bran with a *Bacillus* strain or an *Aspergillus* strain, and fermenting the resulting rice bran for 36 hours or more at a humidity of 60 to 80% and a temperature of 30 to 50° C.

6. The method according to claim 4, wherein the powderizing the raw material comprises powderizing the raw material to a particle size of 40±10 mesh.

7. A health food for inducing defecation and promoting weight loss containing the composition according to claim 1.

* * * * *